US00PP32703P2

(12) United States Plant Patent
Zaiger et al.

(10) Patent No.: US PP32,703 P2
(45) Date of Patent: Dec. 29, 2020

(54) INTERSPECIFIC TREE NAMED 'FLAVORZEE-290'

(50) Latin Name: **Interspecific *Prunus* species**
Varietal Denomination: Flavorzee-290

(71) Applicants: Gary Neil Zaiger, Modesto, CA (US); Leith Marie Gardner, Modesto, CA (US); Grant Gene Zaiger, Modesto, CA (US)

(72) Inventors: Gary Neil Zaiger, Modesto, CA (US); Leith Marie Gardner, Modesto, CA (US); Grant Gene Zaiger, Modesto, CA (US)

( * ) Notice: Subject to any disclaimer, the term of this patent is extended or adjusted under 35 U.S.C. 154(b) by 0 days.

(21) Appl. No.: 16/873,468

(22) Filed: Apr. 20, 2020

(51) Int. Cl.
*A01H 6/74* (2018.01)
*A01H 5/00* (2018.01)

(52) U.S. Cl.
USPC ..... Plt./180

(58) Field of Classification Search
USPC ..... Plt./180
See application file for complete search history.

*Primary Examiner* — Annette H Para

(57) ABSTRACT

A new and distinct variety of interspecific tree. The following features of the tree and its fruit are characterized with the tree budded on 'Nemaguard' Rootstock (non-patented), grown on Handford sandy loam soil with Storie Index rating 95, in USDA Hardiness Zone 9, near Modesto, Calif., with standard commercial fruit growing practices, such as pruning, thinning, spraying, irrigation and fertilization. Its novelty consist of the following combination of desirable features:

1. Tree having a vigorous, upright growth habit.
2. Tree being a regular and productive bearer of medium to large size fruit.
3. Fruit with a high degree of attractive purple skin color.
4. Fruit with very good flavor and eating quality.
5. Fruit with good storage and shipping ability.

1 Drawing Sheet

Botanical designation: Interspecific *Prunus* species.
Variety denomination: 'Flavorzee-290'.

BACKGROUND OF THE VARIETY

Field of the Invention

In the field of plant genetics, we conduct an extensive and continuing plant-breeding program including the organization and asexual reproduction of orchard trees, and of which plums, peaches, nectarines, apricots, cherries, almonds and interspecifics are exemplary. It was against this background of our activities that the present variety of interspecific tree was originated and asexually reproduced by us in our experimental orchard located near Modesto, Stanislaus County, Calif.

PRIOR VARIETIES

Among the existing varieties of interspecific trees, which are known to us, and mentioned herein, 'Flavor Jewel' Interspecific (U.S. Plant Pat. No. 13,502) and the proprietary non-patented interspecific seedling selections '67ZN168', '22MC390', '21MC179', '37ZP705' and '125LX602'.

STATEMENT REGARDING FEDERALLY SPONSORED RESEARCH AND DEVELOPMENT

Not applicable.

ORIGIN OF THE VARIETY

The new and distinct variety of interspecific tree was developed by us in our experimental orchard located near Modesto, Calif. from a first generation cross between our proprietary non-patented interspecific seedling selections '67ZN168' and '37ZP705'. The seed parent (67ZN168) originated from the crosses between our proprietary non-patented interspecific seedling selections '22MC390' and '21MC179'. The pollen parent (37ZP705) originated from the crosses between our proprietary non-patented seedling selections '125LX602' and '21MC179'. A large number of these first generation seedlings were grown and budded to older trees of 'Nemaguard' Rootstock (non-patented) to accelerate rapid fruit production. Under close and careful observation we recognized the desirable tree and fruit characteristics of the present seedling and selected it in 2014 for additional asexual propagation and commercialization.

ASEXUAL REPRODUCTION OF THE VARIETY

In 2014 asexual reproduction of the new and distinct variety of interspecific tree was by budding to 'Nemaguard' Rootstock (non-patented), as performed by us in our experimental orchard located near Modesto, Calif., and shows that reproductions run true to the original tree and all characteristics of the tree and its fruit are established and transmitted through succeeding asexual propagations.

SUMMARY OF THE NEW VARIETY

The present new and distinct variety of interspecific tree is of large size, vigorous, upright growth and a regular and productive bearer of medium to large size, clingstone fruit. The fruit is further characterized by its firm, yellow flesh, attractive purple skin color with very good flavor and eating quality. In comparison to its non-patented interspecific seed parent '67ZN168' the fruit of the new variety is larger in size and is approximately 49 days later in maturity. In comparison to its non-patented interspecific pollen parent the fruit of the new variety is approximately 25 days later in maturity. In comparison to the commercial variety 'Flavor Jewel' Interspecific (U.S. Plant Pat. No. 13,502) the fruit of the new variety is approximately 8 days earlier in maturity.

DESCRIPTION OF THE PHOTOGRAPH

The accompanying color photographic illustration shows typical specimens of the foliage and fruit of the present new interspecific variety. The illustration shows the upper and lower surface of the leaves, an exterior and sectional view of a single fruit divided in its suture plane to show flesh color, pit cavity and the stone remaining in place. The photographic illustration was taken shortly after being picked (shipping ripe) from a 6 year old tree and the colors are as nearly true as is reasonably possible in a color representation of this type.

DESCRIPTION OF THE VARIETY

The following is a detailed botanical description of the new variety of interspecific tree, its flowers, foliage and fruit, as based on observations of 6 year old specimens grown near Modesto, Calif., with color in accordance with Munsell Book of Color published in 1958.

Tree:

*Size*.—Large, usually pruned to 3 to 3.5 meters in height and width for economical harvesting of fruit. Varies with different cultural practices.

*Vigor*.—Vigorous, tree growth of 1.5 to 2 meters the first growing season. Varies with cultural practices, soil type, fertility and climatic conditions.

*Form*.—Upright growth, usually pruned to vase shape.

*Branching habit*.—Upright, crotch angle approximately 35°, increases with heavy crop load.

*Productivity*.—Productive, thinning and spacing of fruit necessary for desired market size fruit. Number of fruit set varies with climatic conditions during blooming period.

*Bearer*.—Regular, has had adequate fruit set 4 consecutive years. No alternate bearing observed.

*Fertility*.—Self sterile, pollinator required.

*Density*.—Medium dense, usually pruned to vase shape to increase air movement and sunlight to enhance fruit color and health of fruit spurs.

*Hardiness*.—Hardy in all stone fruit growing areas of California. Tree grown in USDA Hardiness Zone 9. Winter chilling requirement approximately 700 hours at or below 45° F.

Trunk:

*Size*.—Medium, average circumference 50.8 cm at 25.4 cm above ground on a 6 year old tree.

*Stocky*.—Medium stocky.

*Texture*.—Medium shaggy, roughness increases with age.

*Color*.—Varies from 10YR 3/4 to 10YR 2/2.

Branches:

*Size*.—Large. Average circumference 12.2 cm at 1.2 meters above ground. Crotch angle approximately 35°, increases with heavy crop load.

*Surface texture*.—New growth relatively smooth. Mature growth medium rough, roughness increases with age.

*Lenticels*.—Average number 28 in a 25.8 square cm area. Average length 3.4 mm. Average width 1.9 mm. Color 10YR 4/6.

*Color*.—New growth 2.5GY 6/8. Mature growth varies from 10YR 4/4 to 10YR 2/2, varies with age of growth.

Leaves:

*Size*.—Medium. Average length 110.0 mm. Average width 39.4 mm.

*Form*.—Elliptical.

*Apex*.—Acuminate.

*Base*.—Cuneate.

*Margin*.—Serrate.

*Thickness*.—Medium.

*Surface texture*.—Upper surface relatively smooth, slight indentations over midrib and leaf veins. Lower surface relatively smooth, except for small ridges created by midrib and pinnate venation. Both upper and lower surfaces glabrous.

*Petiole*.—Average length 15.8 mm. Average width 1.5 mm. Longitudinally grooved. Surface — glabrous. Color varies from 5GY 7/4 to 5GY 6/4.

*Glands*.—Type — globose. Size — small. Average length 0.1 mm. Average diameter 0.1 mm. Number varies from 1 to 3, average number 2. Located primarily on the base of the leaf blade and upper portion of the petiole. Color 5GY 6/4.

*Stipules*.—None present at the time of measurement.

*Color*.—Upper surface varies from 7.5GY 4/4 to 7.5GY 3/4. Lower surface varies from 5GY 5/4 to 5GY 4/4. Midvein color varies from 5GY 8/4 to 5GY 7/4.

Flower buds:

*Size*.—Medium to large. Average length 8.5 mm. Average diameter 5.9 mm.

*Hardiness*.—Hardy with respect to California winters.

*Density*.—Medium dense.

*Form*.—Conical, becoming elongated just before opening.

*Pedicel*.—Average length 8.4 mm. Average width 0.9 mm. Surface — glabrous. Color varies from 2.5GY 6/6 to 2.5GY 6/8.

*Color*.—N 9.5/(white).

*Number of buds per spur*.—Varies from 8 to 12, average number 9.

Flowers:

*Blooming period*.—Date of First Bloom Mar. 8, 2019. Date of Petal Fall Mar. 18, 2019, varies slightly with climatic conditions.

*Size*.—Medium to large. Average height 11.5 mm. Average diameter 19.9 mm.

*Petals*.—Normally 5, alternately arranged to sepals. Size — medium to large. Average length 11.5 mm. Average diameter 19.9 mm. Petal apex — rounded. Petal base — truncate. Form — elliptical. Arrangement — overlapping. Margin — sinuate. Color N 9.5/(white). Surface — glabrous.

*Sepals*.—Normally 5, alternately arranged to petals. Size — medium. Average length 4.0 mm. Average width 3.0 mm. Apex — triangular. Margin — entire. Both upper and lower surfaces glabrous. Color — upper surface varies from 5GY 6/6 to 5GY 6/8. Lower surface varies from 5GY 6/8 to 5GY 5/6.

*Stamens*.—Average number per flower 30. Average filament length 8.3 mm. Filament color N 9.5/

(white). Anther color varies from 2.5YR 4/10 to 5YR 5/12. On average, the height of the stamens are even with the petals.

*Pollen*.—Self sterile, pollinator required. Color varies from 2.5Y 7/12 to 2.5Y 6/10.

*Pistil*.—Number — normally one. Average length 10.4 mm. Position of stigma an average of 1.2 mm above anthers. Surface — glabrous. Color varies from 10Y 8/6 to 10Y 7/6.

*Fragrance*.—Heavy aroma.

*Color*.—N 9.5/(white).

*Pedicel*.—Average length 9.0 mm. Average width 1.0 mm. Color 2.5GY 6/10. Surface — glabrous.

Fruit:

*Maturity when described*.—Firm ripe and ready for consumption.

*Date of first picking*.—Aug. 4, 2019.

*Date of last picking*.—Aug. 14, 2019, varies slightly with climatic conditions.

*Size*.—Medium to large. Average diameter axially 65.3 mm. Average transversely in suture plane 63.0 mm. Average weight 162.7 grams, varies slightly with fertility of the soil, amount of thinning and climatic conditions.

*Form*.—Slightly elongated.

*Suture*.—Lipped.

*Ventral surface*.—Lipped.

*Apex*.—Slightly retuse.

*Base*.—Retuse.

*Stem cavity*.—Rounded to slightly elongated in suture plane. Average depth 10.6 mm. Average diameter 7.0 mm.

Stem:

*Size*.—Medium to large. Average length 15.8 mm. Average width 2.7 mm.

*Color*.—Varies from 10YR 4/6 to 7.5YR 4/6.

Flesh:

*Ripens*.—Evenly.

*Texture*.—Firm, meaty.

*Fibers*.—Few, small, tender.

*Firmness*.—Good, comparable to other commercial interspecific varieties.

*Aroma*.—Slight.

*Amydgalin*.—Undetected.

*Eating quality*.—Very good.

*Flavor*.—Very good, good balance between acid and sugar.

*Juice*.—Moderate amount, enhances flavor.

*Acidity*.—Not available.

*Brix*.—Average Brix 20.0°, varies slightly with amount of fruit per tree and climatic conditions.

*Color*.—Varies from 2.5Y 8.5/6 to 2.5Y 8/8.

*Pit cavity*.—Average length 26.6 mm. Average width 19.7 mm. Average depth 7.6 mm. Color varies from 7.5YR 5/6 to 10YR 6/8.

Skin:

*Thickness*.—Medium.

*Surface*.—Slightly waffled.

*Bloom*.—Moderate amount, complete coverage.

*Tendency to crack*.—None.

*Color*.—Ground color varies from 2.5Y 7/4 to 5Y 8.5/4. Overspread with 7.5R 2/8 to 7.5R 2/2.

*Tenacity*.—Tenacious to the flesh.

*Astringency*.—Undetected.

Stone:

*Type*.—Clingstone, medium adherence to flesh.

*Size*.—Medium to large. Average length 25.6 mm. Average width 18.7 mm. Average thickness 13.1 mm.

*Form*.—Obovoid.

*Base*.—Flat.

*Apex*.—Pointed. Average length 1.5 mm.

*Surface*.—Pitted throughout, pits vary from round to elongated.

*Sides*.—Unequal, one side extending further from suture plane.

*Ridges*.—Relatively smooth, extending from base to apex.

*Tendency to split*.—None.

*Color*.—Varies from 7.5YR 6/10 to 7.5YR 6/8, when dry.

Kernel:

*Size*.—Medium. Average length 14.9 mm. Average width 10.4 mm. Average depth 7.0 mm.

*Form*.—Ovate.

*Viability*.—Viable, complete embryo development.

*Skin color*.—Varies from 2.5Y 8.5/6 to 10YR 8/8.

Use:

*Dessert*.—Market — local and long distance.

Keeping quality: Good, held firm in cold storage 3 weeks at 38° to 42° F. without shriveling, internal breakdown of flesh or appreciable loss of flavor.

Shipping quality: Good, showed minimal skin scarring or flesh bruising during picking, packing and shipping trials.

Plant/fruit disease resistance/susceptibility: No specific testing for relative plant/fruit disease resistance/susceptibility has been designed. Under close observation during planting, growing and harvesting of fruit, under normal cultural and growing conditions near Modesto, Calif., no particular plant/fruit disease resistance or susceptibility has been observed. Any variety observed during indexing of plant characteristics with abnormal fungus, bacterial, virus or insect susceptibility is destroyed and eliminated from our breeding program. No atypical resistances/susceptibilities have been noted under normal cultural practices. The present new variety of interspecific tree, its flowers, foliage and fruit herein described may vary in slight detail due to climate, soil conditions and cultural practices under which the variety may be grown. The present description is that of the variety grown under the ecological conditions prevailing near Modesto, Calif.

The invention claimed is:

1. A new and distinct variety of interspecific tree, substantially as illustrated and described.

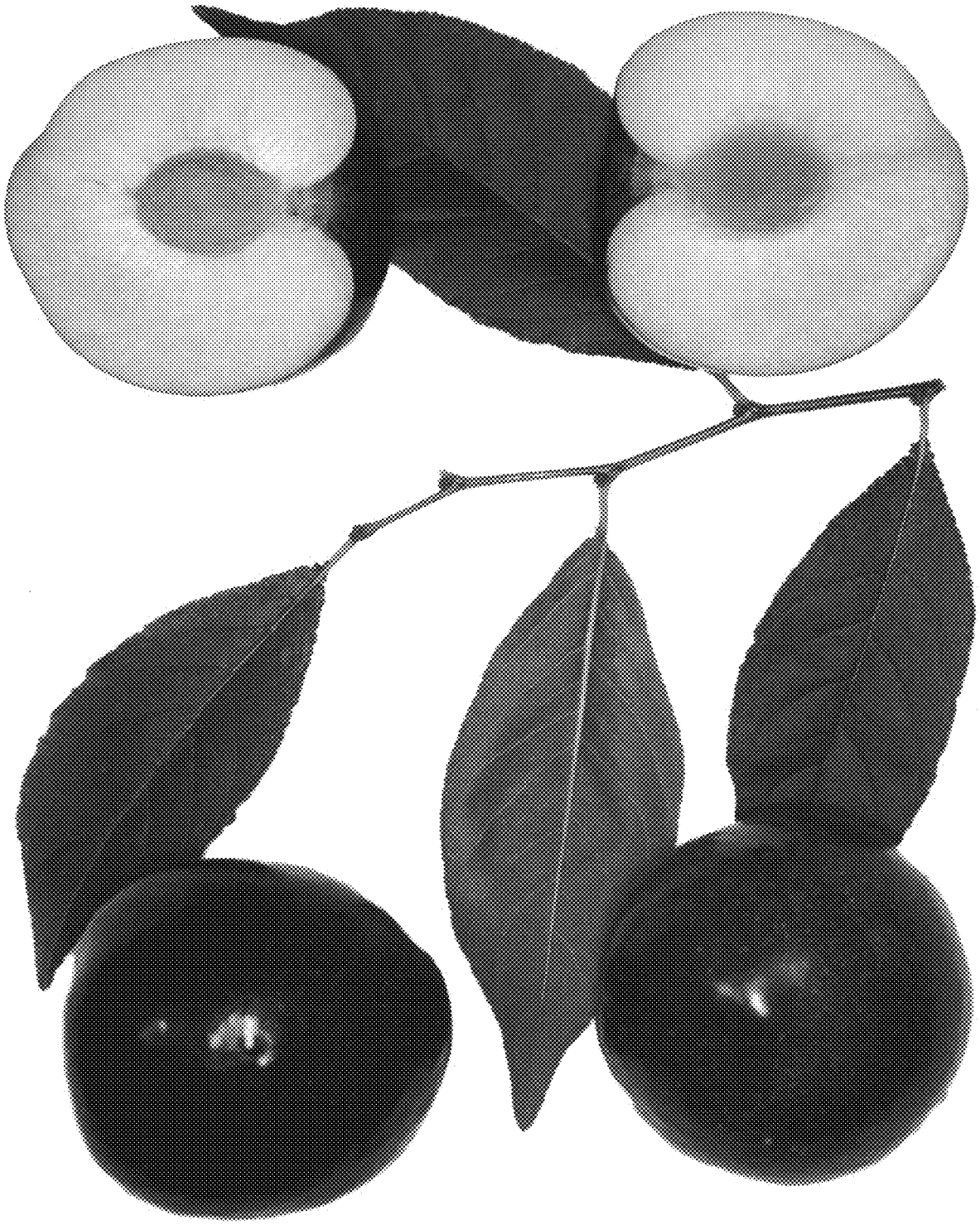

* * * * *